United States Patent [19]

Ogata et al.

[11] Patent Number: 5,596,128
[45] Date of Patent: Jan. 21, 1997

[54] SULFONATING AGENT AND SULFONATION PROCESS

[75] Inventors: Eiji Ogata; Norio Yanase, both of Wakayama; Takayuki Kitahara, Naga-gun, all of Japan

[73] Assignee: Konishi Chemical Ind. Co., Ltd., Wakayama, Japan

[21] Appl. No.: 300,844

[22] Filed: Sep. 6, 1994

Related U.S. Application Data

[63] Continuation of Ser. No. 852,199, filed as PCT/JP91/01372 Oct. 9, 1991, published as WO92/06935 Apr. 30, 1992, abandoned.

[30] Foreign Application Priority Data

Oct. 12, 1990 [JP] Japan .................... 2-273725

[51] Int. Cl.⁶ .................................................. C07C 303/02
[52] U.S. Cl. .................. 562/95; 562/45; 562/58; 562/91; 552/221
[58] Field of Search .................... 852/199; 552/221; 562/95, 91, 45, 58

[56] References Cited

U.S. PATENT DOCUMENTS 3,222,393 12/1965 Rai ............................................. 562/45
3,941,810 3/1976 Koebner .................................... 562/45

OTHER PUBLICATIONS

International Search Report issued in the International application No. PCT/JP91/01372.
Koji Nakanishi et al, Japanese Translation of Morrison & Boyd, *Organic Chemistry*, 2nd Ed.(1968).
Recuel des Travaux Chimiqnes des Rays. Bas, 106(3), 85–103 (1987).
J. Am. Chem. Soc. 23, 236–249 (1901).
J. Chem Soc. 45,148–153, (1884).
Partial translation of Czechoslovakian Patent No: 156, 190 (1974).
Recueil Des Travaux Chimiques Des Pays–Bas, vol. 109, Feb. 1990, Den Haag NL pp. 41–45. H. Cerfontain et al "Acid–catalyzed transfer sulfonation of anisole using over-crowded polymethylbenzenesulfonic acids".
Annales De Chimie –Science Des Materiaux, vol. 4, No. 6, 1969, Paris FR, pp. 497–514. H. Zamarlik "Transsulfonation des amines aromatiques".
Supplementary European Search Report dated Feb. 5, 1993.

*Primary Examiner*—James H. Reamer
*Attorney, Agent, or Firm*—Armstrong, Westerman Hattori, McLeland & Naughton

[57] ABSTRACT

A sulfonating agent represented by the general formula

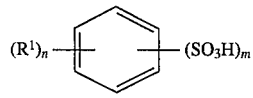

wherein the groups $R^1$ are the same or different and are each a lower alkyl group having 1 to 3 carbon atoms, n is an integer of 3, 4 or 5, m is an integer of 1 or 2, and $n+m \leq 6$, and a process for sulfonating an aromatic compound with use of the sulfonating agent.

12 Claims, No Drawings

SULFONATING AGENT AND SULFONATION PROCESS

This application is a continuation of application Ser. No. 07/825,199, filed as PCT/JP91/01372 Oct. 9, 1991 published as WO92/06935 Apr. 30, 1992, now abandoned.

TECHNICAL FIELD

The present invention relates to sulfonating agents and a sulfonation process, more particularly a process for sulfonating aromatic compounds.

BACKGROUND ART

Conventionally, (concentrated) sulfuric acid, fuming sulfuric acid, chlorosulfonic acid, sulfuric anhydride, adduct of dioxane with $SO_3$, adduct of amine with $SO_3$, etc. are chiefly used as agents for sulfonating aromatic compounds by introducing a sulfonic acid group into the aromatic ring of the compound. However, the use of such agents for sulfonation involves various problems. For example, sulfuric acid or fuming sulfuric acid, when used, produces water as a by-product to result in a reduced conversion. To preclude the reduction of the conversion, an excess of the sulfonating agent needs to be used, consequently producing a large amount of waste acid. On the other hand, use of chlorosulfonic acid or sulfuric anhydride produces no waste acid, whereas these agents have higher sulfonating and oxidating abilities than sulfuric acid and fuming sulfuric acid and therefore produce a sulfone or like by-product or form a colored sulfonated product. The adduct of dioxane or amine with $SO_3$ is not as high as chlorosulfonic acid and sulfuric anhydride in sulfonating ability, but use of the adduct produces a waste acid and encounters difficulty in collecting the adduct.

Aromatic amine compounds are sulfonated by the so-called baking process wherein an acidic sulfate of amine is prepared from the aromatic amine compound and a stoichiometric amount of sulfuric acid and heated in a solid state or in a solvent at a high temperature for dehydration to obtain an aminesulfonic acid. The baking process also has the following problems. The process (solid process) wherein the salt is heated in the solid state to a high temperature is not usable for substances which are liable to oxidation, requires a special reactor and causes marked corrosion to the reactor. On the other hand, the process (solvent process) wherein the salt is heated in the solvent is applicable even to substances which are prone to oxidation, does not require a special reactor but is not substantially amenable to quantity production by a scale-up because if the process is practiced on an enlarged scale, the azeotropic dehydration with use of the solvent, which takes place in a velocity controlling step of the reaction, necessitates a greatly prolonged reaction time and causes oxidation of the product.

DISCLOSURE OF THE INVENTION

An object of the present invention is to provide a sulfonating agent for industrially advantageously sulfonating aromatic compounds without entailing the foregoing problems encountered with the conventional sulfonating agents, and a process for sulfonating aromatic compounds with use of the agent.

More specifically, the sulfonating agent of the present invention is a tri-, tetra- or penta-alkylbenzenesulfonic acid represented by the general formula (I)

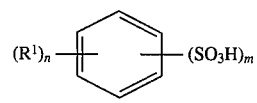

wherein the group $R^1$ are the same or different and are each a lower alkyl group having 1 to 3 carbon atoms, n is an integer of 3, 4 or 5, m is an integer of 1 or 2, and $n+m \leq 6$.

Our research has revealed that when aromatic compounds are sulfonated with the sulfonating agent of the invention represented by the general formula (I), sulfonation proceeds moderately to afford the desired sulfonated product having a sulfonic acid group introduced into the aromatic ring of the compound and substantially free of coloration in a good yield and with a high purity, without producing a waste acid and without forming by-products such as water and undesired oxides or sulfones. Especially when the sulfonating agent of the invention is used for sulfonating aromatic amine compounds, all the drawbacks of the conventional baking process can be overcome. In fact, the use of the present agent does not entail the oxidation reaction to be involved in the solid process or necessitate a special reactor, and readily permits a scale-up operation with use of a usual reactor as desired although the solvent process was difficult to practice on an enlarged scale, consequently giving the desired sulfonated product in a good yield within a short period of time.

The sulfonation reaction of aromatic compounds with the present sulfonating agent is represented by the following equation.

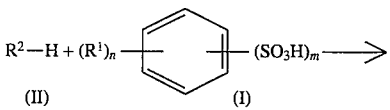

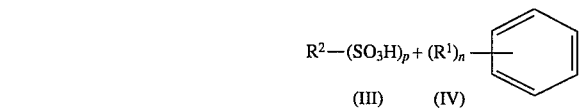

wherein $R^1$, n and m are as defined above, $R^2$ is an aromatic ring having or not having a substituent, H in $R^2$—H is a hydrogen atom attached directly to a carbon atom forming the aromatic ring, and p is the number of sulfonic acid group(s) introduced into the aromatic ring and is usually an integer of 1 or 2.

The sulfonation with the sulfonating agent of the invention attaches a sulfonic acid group directly to a carbon atom forming the aromatic ring of the aromatic compound. The position where the sulfonic acid group is introduced is dependent on the substituent on the aromatic ring. For example in the sulfonation of aromatic amine compounds, the sulfonic acid group is introduced in the para position when substituents are absent in the para position, or in the ortho position when substituents are present in the para position. The reaction proceeds generally stoichiometrically. When the reaction is completed, all the sulfonic acid groups present in the sulfonating agent are introduced into the aromatic compound. The sulfonation reaction of the invention includes a monosulfonation reaction and disulfonation reaction, and the monosulfonation reaction is especially desirable.

The lower alkyl groups defined by $R^1$ in the general formula (I) representing the sulfonating agent for use in the invention includes straight-chain or branched-chain lower alkyl groups having 1 to 3 carbon atoms, i.e., methyl, ethyl, propyl and isopropyl, among which methyl or ethyl is preferable, and methyl is most preferable. The number (n) of alkyl groups is 3 to 5. The number n is preferably 3, that is, trialkylbenzene-sulfonic acids are preferable, among which, trimethylbenzene-sulfonic acids are most preferable. The number (m) of sulfonic acid group(s) is 1 or 2. Monosulfonic acid compounds are especially desirable in which m is 1.

Specific examples of sulfonating agents of the present invention are 1,3,5-trimethylbenzene-2-sulfonic acid, 1,3,5-trimethylbenzene-2,4-disulfonic acid, 1,2,4-trimethylbenzene-5-sulfonic acid, 1,2,4-trimethylbenzene-3-sulfonic acid, 1,2,3-trimethylbenzene-4-sulfonic acid, 1,2,3,4-tetramethylbenzene-5-sulfonic acid, 1,2,3,5-tetramethylbenzene-4-sulfonic acid, 1,2,4,5-tetramethylbenzene-3-sulfonic acid, 1,2,4,5-tetramethylbenzene-3,6-disulfonic acid, 1,2,3,4,5-pentamethylbenzene-6-sulfonic acid, 1,3,5-triethylbenzene-2-sulfonic acid, 1-ethyl-3,5-dimethylbenzene-2-sulfonic acid, 1-ethyl-3,5-dimethylbenzene-4-sulfonic acid, 1-ethyl-3,4-dimethylbenzene-6-sulfonic acid, 1-ethyl-2,5-dimethylbenzene-3-sulfonic acid, 1,2,3,4-tetraethylbenzene-5-sulfonic acid, 1,2,4,5-tetraethylbenzene-3-sulfonic acid, 1,2,3,4,5-pentaethylbenzene-6-sulfonic acid, 1,3,5-triisopropylbenzene-2-sulfonic acid, 1-propyl-3,5-dimethylbenzene-4-sulfonic acid, etc. Preferable among these are compounds substituted with lower alkyls in the ortho positions at both sides of the sulfonic acid group, such as 1,3,5-trimethylbenzene-2-sulfonic acid, 1,2,4,5-tetramethylbenzene-3-sulfonic acid, 1,2,3,5-tetramethylbenzene-4-sulfonic acid, 1,2,3,4,5-pentamethylbenzene-6-sulfonic acid, 1,3,5-trimethylbenzene-2,4-disulfonic acid, 1,3,5-triethylbenzene-2-sulfonic acid, etc. Of these, 1,3,5-trimethylbenzene-2-sulfonic acid is the most preferable. These sulfonating agents of the invention are all known compounds and can be prepared easily by various known processes, for example, by sulfonating an alkylbenzene with sulfuric anhydride, chlorosulfonic acid or the like. It is desirable to use the sulfonating agent of the invention in an anhydrous state.

The aromatic compounds to be sulfonated with the sulfonating agent of the invention include various aromatic compounds which need to be sulfonated and those which have been sulfonated in the prior art. Typical examples of such compounds are given below.

(1) Aromatic amine compounds

Aromatic amine compounds including, for example, aniline, naphthylamine, aminobiphenyl, aminobinaphthyl, aminoanthracene, aminophenanthrene, aminopyrene, aminoanthraquinone, etc. Such aromatic amine compounds are those having no substituent or having one or at least two substituents. Examples of substituents which may be present are lower alkyl, hydroxyl, lower alkoxyl, halogen atom, nitro, carboxyl, sulfonic acid group, etc. Examples of aromatic amine compounds having such a substituent are toluidine, chloroaniline, aminophenol, diaminobenzene, nitroaniline, methoxyaniline, N,N-dimethylaniline, aminobenzoic acid, arlilinesulfonic acid, methylnaphthylamine, chloronaphthylamine, aminonaphthol, nitronaphthylamine, methoxynaphthylamine, aminonaphthoic acid, naphthylaminesulfonic acid, aminoanthracene and the like. Preferable aromatic amine compounds are anilines or naphthylamines having or not having the above substituent.

(2) Aromatic compounds other than aromatic amine compounds

Aromatic compounds not substituted with amino and including, for example, benzene, naphthalene, anthracene, biphenyl, binaphthyl, terphenyl, phenanthrene, pyrene and like aromatic compounds. Such aromatic compounds are those having no substituent or having one or at least two substituents. Examples of substitutents which may be present are lower alkyl, hydroxyl and lower alkoxyl. Examples of other substituents which may be present conjointly with these substituents are halogen atoms, and carboxyl, aldehyde, azo, carbonyl, sulfonic acid and like groups. Examples of aromatic compounds having such substituents are toluene, ethylbenzene, xylene, diethylbenzene, phenol, cresol, xylenol, chlorophenol, methoxybenzene, dihydroxybenzene, phenolsulfonic acid, hydroxybenzaldehyde, hydroxyacetophenone, hydroxyazobenzene, methylnaphthalene, chloronaphthol, naphthol, naphtholsulfonic acid, methylanthracene, hydroxyanthracene and the like. Preferable aromatic compounds are benzenes or naphthalenes having no substituent, or having lower alkyl, hydroxyl or lower alkoxyl as a substituent, or having such a substituent and other substitutent which can be present conjointly therewith.

(3) Aromatic high-molecular-weight compounds

High-molecular-weight compounds having an aromatic ring on the main chain or side chain of a polymer. Examples of such compounds are polystyrene, copolymers of styrene and other monomers copolymerizable therewith, polysulfone, etc., among which polysulfone is desirable.

The sulfonation reaction of the present invention can be effected easily, for example, by reacting the aromatic compound to be sulfonated with the sulfonating agent of the invention with heating in the presence of a solvent.

The sulfonating agents of the present invention can be used singly or in the form of a mixture of at least two of them. The sulfonating agent is used in a stoichiometric to excessive amount or in a smaller amount depending on the sulfonated compound to be obtained. More specifically, the sulfonating agent is used in a stochiometric to slightly excessive amount or in a smaller amount in terms of the number of sulfonic acid groups per mole of the aromatic compound. For example when a sulfonated compound having one sulfonic acid group introduced therein is to be obtained, the sulfonating agent is used in an amount, calculated as the number of sulfonic acid groups therein, of 0.5 to 1.5 times, preferably 0.9 to 1.2 times, the mole number of the aromatic compound to be sulfonated. Further when a sulfonated compound having two sulfonic acid groups introduced therein is to be obtained, the sulfonating agent is used in an amount, calculated as the number of sulfonic acid groups therein, of 1.5 to 3.0 times, preferably 1.8 to 2.4 times, the mole number of the aromatic compound to be sulfonated.

The solvent to be used in the sulfonation process of the invention is not limited specifically but can be any of those which dissolve the aromatic compound to be sulfonated and sulfonating agent and which will not adversely affect the sulfonation reaction. Examples of useful solvents are chloroform, dichloromethane, 1,2-dichloroethane, trichloroethane, tetrachloroethane, trichloroethylene, tetrachloroethylene and like halogenated aliphatic hydrocarbons, dichlorobenzene, trichlorobenzene and like halogenated aromatic hydrocarbons, nitromethane, nitrobenzene and like nitro compounds, trimethylbenzene, tributylbenzene, tetramethylbenzene, pentamethylbenzene and like alkylbenzenes, sulfolane and like heterocyclic compounds, and octane, decane, cyclohexane and like straight-chain, branched-chain or cyclic aliphatic saturated hydrocarbons. These solvents are used singly, or at least two of them are used in admixture. The amount of solvent to be used, which differs with the compound to be sulfonated and is suitably determined, is usually about 1 to about 20 times the amount by weight of the sulfonating agent.

The reaction temperature and time for sulfonation, which also differ with the aromatic compound to be sulfonated and can be suitably determined, are usually about 20° to about 200° C. and about 0.1 to about 15 hours, respectively.

The desired sulfonated product formed separates out from the reaction system in the form of crystals or an oily substance, as it is formed or after the reaction mixture is cooled. Alternatively, the product is obtained as dissolved in the reaction system. The product obtained in such a state can be isolated as a substantially dried free acid, for example, by filtering off the crystalline product, followed by washing with a solvent and drying, by separating the oily product from the other liquid, or by evaporating the solution to dryness to obtain a solid substance. Alternatively, the product can be isolated easily by a usual method, for example, by adding water and, when desired, an alkali, to the reaction mixture to dissolve the sulfonated product and obtain an aqueous phase as separated from a solvent phase, crystallizing the product from the aqueous phase in a usual manner as with an acid or salt and filtering off the crystals. The aqueous phase obtained by the above procedure and containing the sulfonated product can be adjusted to a suitable concentration for use in applications without purification. Thus according to the present invention, the sulfonated product can be isolated in the form of a free acid, or when desired in the form of a salt, with high purity. Moreover, the sulfonated product is almost free of coloration and is therefore usable for various applications without necessitating purification.

On the other hand, the sulfonating agent of the invention is converted to a lower alkylbenzene compound (IV) by the sulfonation reaction by having its group —$SO_3H$ removed as represented by the foregoing reaction equation. After the completion of the reaction, this compound is present as dissolved in the solvent. When the desired sulfonated product is separated off in the form of crystals or an oily substance, the compound remains dissolved in the filtrate or solvent phase, and is thereby separated from the sulfonated product and collected. Alternatively, when the sulfonated product is obtained by evaporating the reaction mixture to dryness, the compound is distilled off along with the solvent, thereby separated from the sulfonated product and collected. When water is added to the reaction mixture for separation as stated above, the alkylbenzene compound is present in the solvent phase and can be easily separated from the sulfonated product for collection. The solvent phase containing the alkylbenzene compound and thus separated is sulfonated as it is or after distillation when so required to regenerate the compound for reuse.

EXAMPLES

The features of the present invention will be further clarified with reference to the following examples.

Example 1

A 1,3,5-trimethylbenzene solution (143 parts) containing 59.5 parts of 1,3,5-trimethylbenzene-2-sulfonic acid was heated to 90° C., and 27.4 parts of toluene was added dropwise to the solution. The resulting solution was maintained at 120° C. for 9 hours for reaction. A sample of the reaction mixture was then collected and analyzed by the HPLC external standard method with the result given below.

Toluene=1.4 parts, conversion=95% (material consumption, the same as hereinafter).

Toluene-4-sulfonic acid=40.9 parts, yield based on consumed toluene=84% (yield based on consumed material, the same as hereinafter).

Toluene-2-sulfonic acid=7.7 parts, yield based on consumed toluene=16%.

Five parts of water was added to the reaction mixture, and the product separating out was filtered off to obtain crystals of the desired sulfonic acid.

Example 2

A 1,2-dichloroethane solution (464 parts) containing 64.8 parts of 1,2,4,5-tetramethylbenzene-3-sulfonic acid was heated to 75° C., and 27.8 parts of toluene was added dropwise to the solution. The resulting solution was maintained under reflux (85° C.) for 10 hours for reaction. A sample was collected from the reaction mixture and analyzed by the HPLC external standard method with the result given below.

Toluene=0.8 part, conversion=97%.

Toluene-4-sulfonic acid=43.9 parts, yield based on consumed toluene=87%.

Toluene-2-sulfonic acid=6.4 parts, yield based on consumed toluene=13%.

The reaction mixture was treated in the same manner as in Example 1 to obtain the desired product.

Example 3

A 1,2-dichloroethane solution (633 parts) containing 69.2 parts of 1,2,3,4,5-pentamethylbenzene-6-sulfonic acid was heated to 70° C., and 27.9 parts of toluene was added dropwise to the solution. The resulting solution was maintained at 85° C. for 1 hour for reaction. A sample was collected from the reaction mixture and analyzed by the HPLC external standard method with the result given below.

Toluene=0.8 part, conversion=97%.

Toluene-4-sulfonic acid=43.0 parts, yield based on consumed toluene=85%.

Toluene-2-sulfonic acid=7.6 parts, yield based on consumed toluene=15%.

The reaction mixture was treated in the same manner as in Example 1 to obtain the desired product.

Example 4

A 1,2-dichlorobenzene solution (250 parts) containing 44.0 parts of 1,3,5-trimethylbenzene-2,4-disulfonic acid was heated to 70° C., and 28.9 parts of toluene was added dropwise to the solution. The resulting solution was maintained at 130° C. for 4 hours for reaction. A sample was collected from the reaction mixture and analyzed by the HPLC external standard method with the result given below.

Toluene=0.9 part, conversion=97%.

Toluene-4-sulfonic acid=44.5 parts, yield based on consumed toluene=85%.

Toluene-2-sulfonic acid=7.9 parts, yield based on consumed toluene=15%.

The reaction mixture was treated in the same manner as in Example 1 to obtain the desired product.

Example 5

Toluene (27.0 parts) was added dropwise at 25° C. to 550 parts of 1,2-dichlorobenzene solution containing 71.0 parts of 1,3,5-triethylbenzene-2-sulfonic acid. The resulting solution was maintained at 80° C. for 4 hours for reaction. A sample was collected from the reaction mixture and analyzed by the HPLC external standard method with the result given below.

Toluene=2.7 parts, conversion=90%.

Toluene-4-sulfonic acid=39.7 pats, yield based on consumed toluene=87%.

Toluene-2-sulfonic acid=5.9 parts, yield based on consumed toluene=13%.

The reaction mixture was treated in the same manner as in Example 1 to obtain the desired product.

Comparative Example 1

(Sulfonation with Concentrated Sulfuric Acid)

Toluene (27.7 parts) was admixed with 31.2 parts of concentrated sulfuric acid, and the mixture was heated at 100° to 110° C. under reflux for 1 hour. A sample was collected from the reaction mixture and analyzed by the HPLC external standard method with the result given below.

Toluene=4.7 parts, conversion=83%.

Toluene-4-sulfonic acid=36.1 parts, yield based on consumed toluene=84%.

Toluene-2-sulfonic acid=6.9 parts, yield based on consumed toluene=16%.

Unreacted sulfuric acid=6.2 parts, conversion=80%.

By-product water=5.1 parts.

In the sulfonation with concentrated sulfuric acid as in the above comparative example, the reaction produces water as a by-product and ceases when the sulfuric acid concentration drops to a certain level, so that toluene, waste acid and water remain in the system and are difficult to separate from the desired product.

Example 6

A 1,2-dichloroethane solution (377.7 parts) containing 51.7 parts of 1,3,5-trimethylbenzene-2-sulfonic acid was maintained at 50° C., a solution containing 23.1 parts of phenol dissolved in 38 parts of 1,2-dichloroethane was added dropwise to the solution over a period of about 10 minutes, and the mixture was heated to 80° C. over a period of about 5 minutes. About 1.5 hours thereafter, an oily substance started to form, but the mixture was allowed to stand at the same temperature for 6 hours for reaction. After the completion of the reaction, the mixture cooled, allowed to stand overnight and filtered to obtain a solidified oily substance in the form of crystals. The crystalline product and filtrate obtained were analyzed by the HPLC external standard method with the following result.

|  | 4-Sulfonic acid | 2-Sulfonic acid | Disulfonic acid | Phenol | Total |
|---|---|---|---|---|---|
| Crystals wt. | 39.7 parts | 0.7 part | 1.0 part | 0.0 part | 41.4 parts |
| Yield (phenol) | 92.8% | 1.6% | 1.6% | 0.0% | 96.0% |
| Filtrate wt. | 0.3 part | 1.2 parts | 0.0 part | 0.1 part | 1.6 parts |
| Yield (phenol) | 0.7% | 2.9% | 0.0% | 0.4% | 4.0% |
| Total wt. | 40.0 parts | 1.9 parts | 1.0 part | 0.1 part | 43.0 parts |
| Yield (phenol) | 93.5% | 4.5% | 1.6% | 0.4% | 100.0% |

Comparative Example 2

Conventional Process (Sulfuric Acid Process)

Phenol (23.2 parts) was melted by heating at about 65° C., and 23.7 parts of concentrated sulfuric acid was added dropwise to the molten phenol over a period of 1 hour. In the meantime, the temperature of the reaction mixture rose from 67° C. to 83° C. The mixture was allowed to stand at 80° C. for 17 hours. From the start of the reaction until the completion thereof, the reaction mixture remained in the form of a uniform solution. During the reaction and on completion of the reaction, samples were collected from the mixture and analyzed by the HPLC external standard method with the result given below.

|  | 4-Sulfonic acid | 2-Sulfonic acid | Disulfonic acid | Phenol | Total |
|---|---|---|---|---|---|
| In 6th hour wt. | 33.4 parts | 5.0 parts | 3.1 parts | 1.3 parts | 42.9 parts |
| Yield (phenol) | 77.8% | 11.6% | 4.9% | 5.7% | 100% |
| On completion wt. | 35.9 parts | 2.1 parts | 3.4 parts | 1.4 parts | 42.8 parts |
| Yield (phenol) | 83.7% | 4.9% | 5.4% | 6.0% | 100% |

Remaining sulfuric acid 1.4 parts (5.4% based on sulfuric acid charge),
Water 4.4 parts.

Thus, the sulfuric acid process produces by-product water and waste acid, which are difficult to separate from the desired product. The reaction required a prolonged period of time and gives the desired product, 4-sulfonic acid, in a low yield.

Examples 7–11

Other compounds were sulfonated in the same manner as in Example 1. The following table shows the results.

| Ex. | Compound to be sulfonated | sulfonating agent | solvent | Temp. (°C.) | Time (hr) | Conversion (%) | Acid ratio of product (%) | Product |
|---|---|---|---|---|---|---|---|---|
| 7 | Naphthalene | Mes_S (1.00) | Mes | 120 | 7 | 92 | 45 | Naphthalene-1-sulfonic acid |
|   |             |              |     |     |   |    | 55 | Naphthalene-2-sulfonic acid |
| 8 | Naphthalene | Mes_S (1.00) | Mes | 160 | 4 | 96 | 19 | Naphthalene-1-sulfonic acid |
|   |             |              |     |     |   |    | 81 | Naphthalene-2-sulfonic acid |
| 9 | 1-Naphthol  | Mes_S (1.00) | EDC | 80  | 18| 99 | 92 | 1-Naphthol-4-sulfonic acid |
|   |             |              |     |     |   |    | 7  | 1-Naphthol-2-sulfonic acid |
|   |             |              |     |     |   |    | 1  | 1-Naphthol-2,4-disulfonic acid |
| 10| 2-Naphthol  | Mes_S (1.00) | EDC | 80  | 10| 97 | 95 | 2-Naphthol-6-sulfonic acid |
|   |             |              |     |     |   |    | 5  | 2-Naphthol-8-sulfonic acid |
| 11| Salicylic acid | Mes_S (1.00) | o-DCB | 120 | 2.5 | 100 | 100 | 5-sulfosalicyclic acid |

Note:
Conversion = Consumption of material
Sulfonating agent Mes_S = 1,3,5-trimethylbenzene-2-sulfonic acid
The value in the parentheses is a mole ratio (sulfonating agent/compound to be sulfonated).
Solvent
Mes = 1,3,5-trimethylbenzene
EDC = 1,2-dichloroethane
o-DCB = 1,2-dichlorobenzene The reaction mixture was cooled to separate out crystals, which were filtered off to obtain a free sulfonic acid. Alternatively, the desired sulfonic acid salt was isolated by adding water to the reaction mixture, neutralizing the mixture with caustic soda to separate off an aqueous solution, and adding common salt to the solution for salting-out or concentrating the solution to dryness.

Example 12

A 1,2-dichloroethane solution (35.5 parts) containing 19.3 parts of polystyrene (30,000 in average molecular weight) was added at 25° C. to 75.5 parts of a 1,2-dichloroethane solution containing 22.0 parts of 1,3,5-trimethylbenzene-2-sulfonic acid. The mixture was heated to 88° C. (reflux state) over a period of about 15 minutes and maintained in this state at 88° C. For 17 hours for reaction. The mixture was in the form of a uniform solution in the initial stage of the reaction but a solid became separated off during the reaction. After the completion of the reaction, the mixture was cooled, and a polymer separating out from the solution was isolated. When analyzed, the polymer was found to exhibit an absorption peculiar to sulfonic acid by IR absorption spectrum. When water was added to the polymer, the polymer was soluble in water.

Water was added to the reaction mixture to obtain a solution, which was neutralized with caustic soda. A solvent phase separated off was discarded to obtain an aqueous solution of sulfonated polymer.

Example 13

A 1,2-dichloroethane solution (120.8 parts) containing 20.2 parts of 1,3,5-trimethylbenzene-2-sulfonic acid was heated to 50° C., 316 parts of 1,2-dichloroethane solution containing 44.3 parts of polysulfone (P3500, product of Amoco Performance Products, Inc.) was added to the solution and the mixture was heated to 80° C. over a period of about 10 minutes. The mixture was then allowed to stand at 80° C. for 7 hours for reaction. Although the mixture was in the form of a uniform solution in the initial stage of the reaction, a solid became separated off during the reaction. After the completion of the reaction, the mixture was cooled, and a polymer separating out from the solution was isolated. When analyzed, the polymer was found to exhibit an absorption peculiar to sulfonic acid by IR absorption spectrum. When water was added to the polymer, the polymer was soluble in water.

The reaction mixture was treated in the same manner as in Example 12, giving an aqueous solution of sulfonated polymer.

Example 14

A 379 g quantity of 1,2-dichlorobenzene solution containing 50.9 g (254 mmols) of 1,3,5-trimthylbenzene-2-sulfonic acid was heated to 60° C., and 31.3 g (254 mmols) of 4-methoxyaniline was placed into the solution. The resulting solution was maintained under reflux (177 to 8° C.) for 8 hours for reaction. Subsequently, a sample was collected from the reaction mixture and analyzed by the HPLC external standard method with the result given below.

4-Methoxyaniline=1.0 g (8 mmols), conversion=97%. 4-Methoxyaniline-2-sulfonic acid=48.5 g (239 mmols), yield based on consumed 4-methoxyaniline=97%.

HPLC area percentage PMSPAOS/PADS=99.3/0.3/0.4

(Note: PAMS=4-methoxyaniline-2-sulfonic acid, PAOS=4-methoxyaniline-3-sulfonic acid, PADS=4-methoxyanilinedisulfonic acid, the same as hereinafter).

A 200 g quantity of water was added to the reaction mixture, followed by neutralization with caustic soda to dissolve the sulfonic acid with the water and remove a solvent phase as separated from an aqueous phase. The desired sulfonic acid was separated out from the aqueous phase in the form of crystals using sulfuric acid.

Example 15

A 2080 kg quantity of 1,2-dichlorobenzene solution containing 489 kg (2.44 kmols) of 1,3,5-trimethylbenzene-2-sulfonic acid was placed into a 3000-liter reactor lined with glass and equipped with a reflux condenser and a water separator, and heated to 60° C. A 300 kg quantity (2.44 kmols) of 4-methoxyaniline was then placed into the reactor. The resulting solution was maintained under reflux (177° to 178° C.) for 9 hours for reaction. A sample was collected from the reaction mixture and analyzed by the HPLC external standard method with the result given below.

4-Methoxyaniline=9 kg (0.07 kmol), conversion=97%.

4-Methoxyaniline-2-sulfonic acid=461 kg (2.27 kmols), yield based on consumed 4-methoxyaniline=96%.

HPLC area percentage PAMS/PAOS/PADS=99.1/0.7/0.2.

The reaction mixture was treated in the same manner as in Example 14 to obtain crystals of the sulfonic acid.

Comparative Example 3

The reaction of Example 15 was conducted by the conventional sulfuric acid baking process.

A 303 kg quantity (2.46 kmols) of 4-methoxyaniline was dissolved in 1560 kg of 1,2-dichlorobenzene in a 3000-liter reactor having a glass lining and equipped with a reflux condenser and a water separator, 241 kg (2.41 kmols) of concentrated sulfuric acid (98.0%) was added to the solution at 80° C. over a period of about 6 hours, and the mixture was aged for 1 hour and heated to about 180° C. Water and solvent azeotropically distilled were condensed and separated off, and the solvent phase only was returned to the reaction system during reaction. Completion of distillation of water required 26 hours. A sample was then collected from the reaction mixture and analyzed by the HPLC external standard method with the following result.

4-Methoxyaniline=61 kg (0.50 kmols), conversion=80%.

4-Methoxyaniline-2-sulfonic acid=352 kg (1.73 kmols), yield based on consumed 4-methoxyaniline=88%.

HPLC area percentage PAMS/PAOS/PADS=95/3/2.

When the sulfuric acid baking process was conducted on the above scale, the reaction required a long period of time, resulted in a low conversion despite the high reaction temperature and gave an increased impurity content to the product.

Example 16

A 1,2-dichlorobenzene solution (284.3 parts) containing 33.2 parts of 1,3,5-trimethylbenzene-2-sulfonic acid was heated to 55° C., 22.9 parts of 2-nitroaniline was added to the solution, and the mixture was heated to 160° C. over a period of about 20 minutes. The mixture was allowed to stand at 160° C. for 4 hours for reaction. A sample of the resulting reaction mixture was analyzed by the HPLC external standard method with the following result.

dissolve the sulfonic acid with the water and remove a solvent phase as separated from an aqueous phase. The aqueous phase was subjected to salting-out with common salt, giving the desired sodium salt of sulfonic acid in the form of crystals.

Comparative Example 4

(Sulfuric Acid Baking Process)

A 1,2-dichlorobenzene solution (148 parts) containing 24 7 parts of 2-nitroaniline was heated to 45° C., and 17.1 parts of concentrated sulfuric acid was added to the solution at 40° C. over a period of about 30 minutes, followed by aging at 40° C. for 1 hour and then by heating. During heating, the mixture bubbled up vigorously at about 170° C. and assumed a hazardous state, so that the reaction was discontinued. A sample was collected from the reaction mixture and analyzed by the HPLC external standard method, which revealed that the conversion to 2-nitroaniline-4-sulfonic acid was about 20%.

Comparative Example 5

(Sulfuric Acid Baking Process)

2-Nitroaniline (20.0 parts) was admixed with 30 parts of diphenylsulfone, 14.4 parts of concentrated sulfuric acid was added dropwise to the mixture, and the resulting mixture was maintained at 150° C. for 10 hours for reaction. When analyzed by the HPLC external standard method, the reaction mixture obtained gave the following result.

Remaining 2-nitroaniline=2.4 parts, conversion 88%.

2-Nitroalinine-4-sulfonic acid=24.9 parts, yield based on consumed 2-nitroaniline=90%.

The conventional baking process with use of sulfuric acid permits decomposition and entails a hazard at a high reaction temperature as observed in Comparative Example 4. Further when the reaction is conducted at a relatively low temperature as in Comparative Example 5, the reaction requires a longer period of time and results in a low yield.

Examples 17–19

Other compounds were sulfonated in the same manner as in Example 11. The table given below shows the results.

| Ex. | Compound to be sulfonated | Sulfonating agent | Solvent | Temp. (°C.) | Time (hr) | Conversion (%) | Acid ratio of product (%) | Product |
|---|---|---|---|---|---|---|---|---|
| 17 | Aniline | Mes_S (2.00) | TCB | 180 | 6 | 100 | 97 | Aniline-2,4-disulfonic acid |
|  |  |  |  |  |  |  | 3 | Aniline-4-sulfonic acid |
| 18 | 3,4-Dichloroaniline aniline | Mes_S (1.00) | o-DCB | 180 | 4 | 96 | 100 | 3,4-Dichloroaniline-6-sulfonic acid |
| 19 | 1-Aminoanthraquinone | Mes_S (1.20) | o-DCB | 150 | 6 | 95 | 99 | 1-Aminoanthraquinone-2-sufonic acid |

Note:
Conversion = consumption of material
Sulfonating agent Mes_S = 1,3,5-trimethylbenzene-2-sulfonic acid
The value in the parentheses is a mole ration.
Solvent
o-DCB = 1,2-dichlorobenzene
TCB = trichlorobenzene Remaining 2-nitroaniline=0.7 part, conversion=97%.

2-Nitroaniline-4-sulfonic acid=34.0 parts, yield based on consumed 2-nitroaniline=97%.

A 200 g quantity of water was added to the reaction mixture, followed by neutralization with caustic soda to Each of these reaction mixtures was treated in the same manner as in Example 14 or 16 to obtain the sulfonic acid or sodium salt thereof in the form of crystals.

We claim:

1. A process for sulfonating an aromatic compound characterized in that the aromatic compound is sulfonated with an anhydrous sulfonating agent in the absence of a catalyst and in an organic solvent selected from the group consisting of halogenated aliphatic hydrocarbons, halogenated aromatic hydrocarbons, nitro compounds, straight-chain aliphatic saturated hydrocarbons, branched-chain aliphatic saturated hydrocarbons and cyclic aliphatic saturated hydrocarbons; said sulfonating agent represented by the general formula

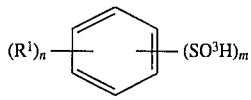

wherein the groups $R^1$ are the same or different and are each a lower alkyl group having 1 to 3 carbon atoms, n is an integer of 3, 4 or 5, m is an integer of 1 or 2 and $n+m \leq 6$.

2. A sulfonating process as defined in claim 1 wherein $R^1$ is methyl or ethyl.

3. A sulfonating process as defined in claim 2 wherein $R^1$ is methyl.

4. A sulfonating process as defined in claim 1 wherein n is 3.

5. A sulfonating process as defined in claim 1 wherein m is 1.

6. A sulfonating process as defined in claim 1 wherein the sulfonating agent is at least one compound selected from the group consisting of 1,3,5-trimethylbenzene-2-sulfonic acid, 1,2,4,5-tetramethylbenzene-3-sulfonic acid, 1,2,3,5-tetramethylbenzene-4-sulfonic acid, 1,2,3,4,5-pentamethylbenzene-6-sulfonic acid, 1,3,5-trimethylbenzene-2,4-disulfonic acid and 1,3,5-triethylbenzene-2-sulfonic acid.

7. A sulfonating process as defined in claim 6 wherein the sulfonating agent is 1,3,5-trimethylbenzene-2-sulfonic acid.

8. A sulfonating process as defined in claim 1 wherein the aromatic compound is an aromatic amine compound.

9. A sulfonating process as defined in claim 1 wherein the aromatic compound is an aromatic compound not substituted with amino.

10. A sulfonating process as defined in claim 1 wherein the aromatic compound is an aromatic high-molecular-weight compound.

11. A sulfonating process as defined in claim 2 wherein n is 3.

12. A sulfonating process as defined in claim 2 wherein m is 1.

* * * * *